(12) United States Patent
Kotwal

(10) Patent No.: US 7,638,481 B2
(45) Date of Patent: Dec. 29, 2009

(54) TREATMENT OF SPINAL CORD INJURY

(75) Inventor: Girish J. Kotwal, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 374 days.

(21) Appl. No.: 10/570,402

(22) PCT Filed: Sep. 3, 2004

(86) PCT No.: PCT/US2004/028794

§ 371 (c)(1),
(2), (4) Date: Nov. 20, 2006

(87) PCT Pub. No.: WO2005/023195

PCT Pub. Date: Mar. 17, 2005

(65) Prior Publication Data

US 2007/0190644 A1 Aug. 16, 2007

Related U.S. Application Data

(60) Provisional application No. 60/500,667, filed on Sep. 5, 2003.

(51) Int. Cl.
*A61K 39/275* (2006.01)
*A61K 39/285* (2006.01)
*A61K 35/76* (2006.01)
*A61K 38/16* (2006.01)

(52) U.S. Cl. .......................... 514/2; 514/12; 424/186.1; 424/232.1

(58) Field of Classification Search ...................... None
See application file for complete search history.

(56) References Cited

U.S. PATENT DOCUMENTS 6,140,472 A * 10/2000 Rosengard et al. ....... 530/387.3

OTHER PUBLICATIONS

Guidelines for the Management of Acute Cervical Spine and Spinal Cord Injuries: Chapter 9. Pharmacological Therapy after Acute Cervical Spinal Cord Injury. Neurosurgery Online, vol. 50(3) Supplement, Mar. 2002, pp. S63-S72.*
Uvarova et al (Virus Research 81:39-45, 2001).*
Miller et al (Virology 229:126-133, 1997).*
Hicks et al (Journal of Neurotrama 19:705-714, 2002).*
Massung et al., "Terminal Region Sequence Variations in Variola Virus DNA," *Virology*, 1996, 221:291-300.
McDonald, "Repairing the Damaged Spinal Cord," *Scientific American*, 1999, 281:64-73.
McKenzie et al., "Regulation of Complement Activity by Vaccinia Virus Complement-Control Protein," *J. Infect. Dis.*, 1992, 166:1245-1250.
Miller et al., "Severe and Prolonged Inflammatory Response to Localized Cowpox Virus Infection in Footpads of C5-Deficient Mice: Investigation of the Role of Host Complement in Poxvirus Pathogenesis," *Cell. Immunol.*, 1995, 162:326-332.

Miller et al., "The Cowpox Virus-Encoded Homolog of the Vaccinia Virus Complement Control Protein in an Inflammation Modulatory Protein," *Virology*, 1997, 229:126-133.
Popovich et al., "Cellular Inflammatory Response After Spinal Cord Injury in Sprague-Dawley and Lewis Rats," *J. Comp. Neurol.*, 1997, 377:443-464.
Popovich et al., "Depletion of Hematogenous Macrophages Promotes Partial Hindlimb Recovery and Neuroanatomical Repair after Experimental Spinal Cord Injury," *Exp. Neurol.*, 1999, 158:351-365.
Popovich and Hickey, "Bone Marrow Chimeric Rats Reveal the Unique Distribution of Resident and Recruited Macrophages in the Contused Rat Spinal Cord," *J. Neuropathol. Exp. Neurol.*, 2001, 60(7):676-685.
Popovich et al., "The Neuropathological and Behavioral Consequences of Intraspinal Microglial/Macrophage Activation," *J. Neuropathol. Exp. Neurol.*, 2002, 61(7):623-633.
Reynolds et al., "Heparin Binding Activity of Vaccinia Virus Protein Confers Additional Properties of Uptake and by Mast Cells and Attachment to Endothelial Cells," *Advances In Animal Virology*, 1998, Jameel and Villarreal (eds.), Science Publishers, pp. 337-342.
Reynolds et al., "Vaccinia Virus Complement Control Protein Modulates Inflammation Following Spinal Cord Injury," *Ann. N.Y. Acad. Sci.*, 2003, 1010:534-539.
Reynolds et al., "Vaccinia Virus Complement Control Protein Reduces Inflammation and Improves Spinal Cord Integrity Following Spinal Cord Injury," *Ann. N.Y. Acad. Sci.*, 2004, 1035:165-178.
Rosengard et al., "Variola virus immune evasion design: Expression of a highly efficient inhibitor of human complement," *Proc. Natl. Acad. Sci. USA*, 2002, 99(13):8808-8813.
Smith et al., "Conserved Surface-Exposed K/R-X-K/R Motifs and Net Positive Charge on Poxvirus Complement Control Proteins Serve as Putative Heparin Binding Sites and Contribute to Inhibition of Molecular Interactions with Human Endothelial Cells: a Novel Mechanism for Evasion of Host Defense," *J. Virol.*, 2000, 74(12):5659-5666.
Uvarova and Shchelkunov, "Species-specific differences in the structure of orthopoxvirus complement-binding protein," *Virus Research*, 2001, 81:39-45.
Vasquez et al., "Spinal Prostaglandins Are Involved in the Development But Not the Maintenance of Inflammation-Induced Spinal Hyperexcitability," *J. Neurosci.*, 2001, 21(22):9001-9008.
Watanabe et al., "Differential Activation of Microglia After Experimental Spinal Cord Injury," *J. Neurotrauma*, 1999, 16(3):255-265.
Anderson, "Mechanisms and pathways of inflammatory responses in CNS trauma: spinal cord injury," *J. Spinal Cord Med.*, 2002, 25:70-79.
Bracken, "Methylprednisolone and Acute Spinal Cord Injury: An Update of the Randomized Evidence," *Spine*, 2001, 26(24S):S47-S54.
Dumont et al., "Acute Spinal Cord Injury, Part I: Pathophysiologic Mechanisms," *Clin. Neuropharmacol.*, 2001, 24(5):254-264.
Farooque et al., "Improved recovery after spinal cord trauma in ICAM-1 and P-selectin knockout mice," *NeuroReport*, 1999, 10:131-134.

(Continued)

*Primary Examiner*—Mary E Mosher
(74) *Attorney, Agent, or Firm*—Fish & Richardson P.C.

(57) ABSTRACT

The present invention relates to the treatment of spinal cord injury with a vaccinia virus complement control protein (VCP).

14 Claims, 4 Drawing Sheets

OTHER PUBLICATIONS

Fitch et al., "Cellular and molecular mechanisms of glial scarring and progressive cavitation: in vivo and in vitro analysis of inflammation-induced secondary injury after CNS trauma,"1999, J. Neuroscience, 19:8182-8198.

Goebel et al., "The Complete DNA Sequence of Vaccinia Virus," *Virology*, 1990, 179:247-266.

Guth et al., "Key role for pregnenolone in combination therapy that promotes recovery after spinal cord injury," *Proc. Natl. Acad. Sci. USA*, 1994, 91:12308-12312.

Hurlbert, "Methylprednisolone for acute spinal cord injury: an inappropriate standard of care," *J. Neurosurg.* (Spine 1), 2000, 93:1-7.

Hurlbert, "The Role of Steroids in Acute Spinal Cord Injury: An Evidence-Based Analysis," *Spine*, 2001, 26(24S):S39-S46.

Jha and Kotwal, "Vaccinia complement control protein: Multi-functional protein and a potential wonder drug," *J. Biosci.*, 2003, 28(3):265-271.

Keeling et al., "Local neutrophil influx following lateral fluid-percussion brain injury in rats is associated with accumulation of complement activation fragments of the third component (C3) of the complement system," *J. Neuroimmunol.*, 2000, 105:20-30.

Kotwal and Moss, "Vaccinia virus encodes a secretory polypeptide structurally related to complement control proteins," *Nature*, 1988, 335:176-178.

Kotwal et al., "Mapping and Insertional Mutagenesis of a Vaccinia Virus Gene Encoding a 13,800-Da Secreted Protein," *Virology*, 1989, 171:579-587.

Kotwal et al., "Inhibition of the Complement Cascade by the Major Secretory Protein of Vaccinia Virus," *Science*, 1990, 250:827-830.

Kotwal et al., "The inflammation modulatory protein (IMP) of cowpox virus drastically diminishes the tissue damage by down-regulating cellular infiltration resulting from complement activation," *Mol. Cell. Biochem.*, 1998, 185:39-46.

Kotwal et al., "Vaccinia virus complement control protein is a virokine with lysozyme-like heparin-binding activity: possible implications in prolonged evasion of host immune response," *Proc. 10th Intl. Cong. Immunol.*, Nov. 1-6, 1998, New Delhi, India pp. 315-320.

Lacroix et al., "Delivery of Hyper-Interleukin-6 to the Injured Spinal Cord Increases Neutrophil and Macrophage Infiltration and Inhibits Axonal Growth," *J. Comp. Neurol.*, 2002, 454:213-228.

Liu et al., "Heme Oxygenase-1 Expression after Spinal Cord Injury: The Induction in Activated Neutrophils," *J. Neurotrauma*, 2002, 19(4):479-490.

Massung et al., "Analysis of the Complete Genome of Smallpox Variola Major Virus Strain Bangladesh-1975," *Virology*, 1994, 201:215-240.

\* cited by examiner

FIG. 3

| | Inhibition of Hemolysis | Heparin Binding Activity | K+R | %K+R | pI | # of Putative Sites (K/R X K/R) |
|---|---|---|---|---|---|---|
| VCP/IMP/SPICE | + | + | 23 | 9.43 | 8.80 | 4 |
| MPV Homolog of VCP | + | N/D | 16 | 8.00 | 7.22 | 3 |
| rVCP | + | + | 23 | 9.43 | 8.80 | 4 |
| rVCP SCR (2,3,4) | – | + | 16 | 8.79 | 7.22 | 2 |
| rVCP SCR (1,2) | – | + | 12 | 9.60 | 7.00 | 3 |
| rVCP SCR (2,3) | – | – | 7 | 5.83 | 4.41 | 1 |
| rVCP SCR (3,4) | – | + | 11 | 9.24 | 9.08 | 1 |

Short Consensus Repeats (SCR)

TREATMENT OF SPINAL CORD INJURY

CROSS-REFERENCE TO RELATED APPLICATIONS

This application is a National Stage application under 35 U.S.C. §371 and claims benefit under 35 U.S.C. §119(a) of International Application No. PCT/US04/28794 having an International Filing Date of Sep. 3, 2004, which claims the benefit of priority of U.S. Application No. 60/500,667, having a filing date of Sep. 5, 2003.

TECHNICAL FIELD

The present invention relates to the treatment of spinal cord injury with a Poxvirus-encoded complement inhibiting protein such as vaccinia virus complement control protein (VCP).

BACKGROUND

Every year in the United States, more than 10,000 people experience spinal cord injury (SCI), with an estimated 250,000 of those cases sufficiently severe to require wheelchair use. A majority of SCI patients are injured while under the age of 30 years and will often experience a normal lifespan, leading to extremely high medical costs over the course of a lifetime.

SCI is an extremely difficult condition to understand and manage in a clinical setting due to the multitude of injury mechanisms involved. In addition to the primary injury, it is thought that a complex array of secondary injury mechanisms account for the progression of damage from the central gray matter to the surrounding white matter that begins within minutes and persists long after primary injury. After several days to weeks, the initial injury can expand in size, leading to a scar-encapsulated cavity many times the size of the original lesion. The cavity is bounded by abnormally proliferating glial cells and primarily astrocytes, which can form a physical barrier to any potential neuronal regeneration. Suspected secondary injury mechanisms include hemorrhage, ischemia-reperfusion, excito-toxicity, demyelination, calcium mediated injury, disturbances in mitochondrial function, apoptosis and/or necrosis of neurons and oligodendrocytes, and inflammation.

Currently, only one therapeutic agent, methylprednisolone (MP), is widely considered standard therapy after traumatic SCI. MP is a synthetic glucocorticosteroid that has been subjected to several large-scale human clinical trials and showed minor clinical benefits when administered within 48 hours of SCI. However, questions regarding MP's efficacy persist due to controversy surrounding study design and analysis/interpretation of data from clinical trials. Therefore, continued investigation and evaluation of potential therapeutic agents for traumatic SCI is paramount. Accordingly, there is a need for methods to treat SCI.

SUMMARY OF THE INVENTION

In one aspect, the invention provides for methods of treating a patient having a spinal cord injury. Such methods include administering to the patient an effective amount of Poxvirus-encoded complement inhibiting protein and a pharmaceutically-acceptable carrier. Typically, the effective amount of the Poxvirus-encoded complement inhibiting protein treats at least one symptom associated with the spinal cord injury. As used herein, "treating" refers to ameliorating at least one symptom of a rheumatic disease, or curing and/or preventing the development of a rheumatic disease or condition.

In certain embodiments, administration of the Poxvirus-encoded complement inhibiting protein delays and/or prevents the onset of at least one symptom of the spinal cord injury. In other embodiments, administration of Poxvirus-encoded complement inhibiting protein reduces spinal cord damage associated with the spinal cord injury, reduces inflammation associated with the spinal cord injury, and/or reduces loss of motor function associated with the spinal cord injury.

In some embodiments, the Poxvirus-encoded complement inhibiting protein is VCP (e.g., recombinant VCP), IMP, smallpox complement inhibiting protein, monkeypox complement inhibiting protein, or variola virus complement inhibiting protein.

In some embodiments, the Poxvirus-encoded complement inhibiting protein can be administered intraperitoneally. In other embodiments, the Poxvirus-encoded complement inhibiting protein can be administered into the spinal cord area. In addition, the Poxvirus-encoded complement inhibiting protein can be administered in multiple administrations. The Poxvirus-encoded complement inhibiting protein also can be administered in combination with at least one additional agent such as a nonsteroidal anti-inflammatory drug (NSAID), or a corticosteroid.

In another aspect, the invention provides for methods of treating a patient having a spinal cord injury. Such methods include administering to the patient an effective amount of Poxvirus-encoded complement inhibiting protein and a pharmaceutically-acceptable carrier, wherein the Poxvirus-encoded complement inhibiting protein is selected from the group consisting of VCP, TIP, monkeypox complement inhibiting protein, smallpox complement inhibiting protein, and variola virus complement inhibiting protein. Typically, the effective amount of the Poxvirus-encoded complement inhibiting protein treats at least one symptom associated with the spinal cord injury.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

Figure 3:
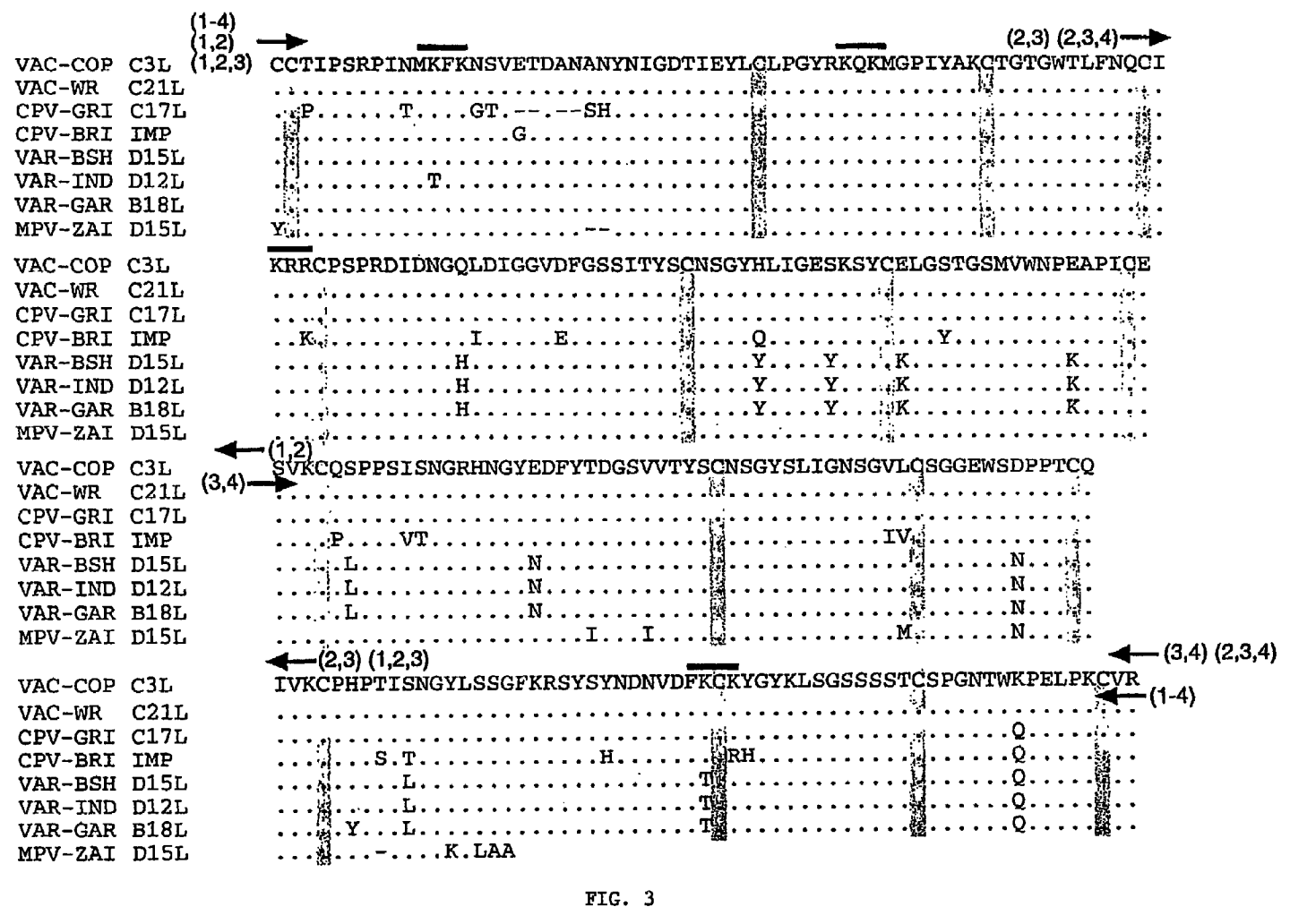

FIG. 3 is a sequence alignment including termini of rVCP constructs and putative heparin binding sites. Multiple alignment of the four short consensus repeats (SCR) from the following orthopoxviruses: vaccinia virus, Copenhagen strain (VAC-COP; SEQ ID NO:1) (Goebel et al., 1990, *Virology*, 179: 247-263), vaccinia virus, western reserve strain (VAC-WR; SEQ ID NO:2) (Kotwal et al., 1989, *Virology*, 171: 579-587), cowpox virus, Russian isolate from human patient (CPV-GRI; SEQ ID NO:3) (Schelkunov et al., 1998, *Virology*, 243:432-460), cowpox virus, Brighton strain (CPV-BRI; SEQ ID NO:4) (Miller et al., 1995, *Cell Immunol.*, 162:326-332), variola virus, Bangladesh strain (VAR-BSH; SEQ ID NO:5) (Massung et al., 1994, *Virology*, 201:215-240), variola major virus, Indian strain (VAR-IND; SEQ ID NO:6) (Schelkunov et al., 1998, *Virology*, 243:432-460) variola minor virus, alastrim Garcia strain (VAR-GAR; SEQ ID NO:7) (Massung et al., 1996, *Virology*, 221:291-300), and monkeypox virus, isolated from a human patient from Zaire in 1996 (MPV-ZAI; SEQ ID NO:8). The putative heparin binding sites (K/R-X-K/R) are marked with solid bars; arrows indicated the termini rVCP constructs; and the cysteines are highlighted.

FIG. 4 depicts a structure-function summary table of VCP, VCP homologues, and rVCPs. VCPIMP/SPICE, MPV homologue of VCP, recombinant VCP, and four recombinant segments of VCP are shown above, along with whether they are able to inhibit hemolysis of sensitized sheep red blood cells and/or bind heparin (IMP=inflammation modulatory protein). Also listed are the number of positively charged amino acids (K+R) found in the protein, percentage of positively charged amino acids (% K+R) making up the protein, pI of the protein, and number of putative heparin binding sites found on the surface of the protein.

DETAILED DESCRIPTION OF THE INVENTION

Utilizing a common animal model of contusion SCI, motor function recovery tests, and immunochemical stains, the effects of a Poxvirus-encoded complement inhibiting protein, VCP, injected into spinal cord tissue following injury was evaluated. Results demonstrate that VCP administration inhibits macrophage infiltration, reduces spinal cord destruction, and improves hindlimb function, establishing the use of Poxvirus-encoded complement inhibiting proteins as an agent for the treatment of SCI.

Poxvirus-Encoded Complement Inhibiting Proteins

The vaccinia virus major secretory protein, referred to as the vaccinia virus complement control protein (VCP), is a Poxvirus-encoded complement inhibiting protein. VCP contains four short consensus repeats that are most similar in sequence (38% identity) to the first four repeats of C4b binding protein, one of the inhibitors of classical complement pathway. Infected cells secrete VCP after cleavage of signal peptide and can inhibit the classical as well as alternate complement pathway. VCP blocks the complement pathway by binding to the third and fourth complement components and by blocking the formation of the C3-convertase as well as by accelerating the decay of the convertase. In addition VCP has been shown to cleave C3b in the presence of factor I to iC3b. VCP is a 35 kD protein which is made up of 243 amino acid residues.

Structurally, VCP consists of four short consensus repeats (SCRs) which bear 38, 35, 31% amino acid identity to C4b-BP, MCP and DAF respectively. Apart from complement regulation, VCP shares another common property with other complement regulators, for example, MCP, DAF, and CR1. This common property is cell-surface association, although the mechanism of surface association is different. VCP has a strong heparin binding ability. It has two heparin binding sites on modules 1 and 4 respectively. As stated before, VCP is an extended molecule. Involvement of regions of module 1 in heparin binding and complement inhibition in VCP indicates that heparin binding function of module 4 is probably more important in cell-surface association.

VCP is a secreted inflammation modulatory protein possessed by the vaccinia virus, a member of the poxvirus family. VCP was identified in 1988 and was found to inhibit the classical and alternative pathways of the complement cascade, a system of more than 30 proteins involved in the innate (nonspecific) immune response. Because of the series of protein cleavages that occur when complement is activated, several potent inflammatory mediators such as C3a, C4a, and C5a are released. Experiments have shown that VCP possesses the ability to inhibit the complement cascade in the early stages of activation, thereby preventing release of inflammatory proteins and enabling the virus to escape detection by the host immune system.

It is important to realize that a seemingly minute degree of neuronal sparing or regeneration could result in a significantly improved quality of life, for voluntary muscle control can occur when only 5%-10% of neurons remain intact through a lesioned segment of the spinal cord. Thus, treatment with VCP or a homologue thereof need only have a minimal effect on neuronal sparing or regeneration to be useful.

The success of the Poxvirus family of viruses is due, in no small part, to its collective ability to encode proteins that subvert the host immune systems. VCP, the major secretory protein of vaccinia virus, is one such molecule. Poxvirus-encoded complement inhibiting proteins, including VCP, are related both structurally and functionally to human C regulatory molecules. Another Poxvirus-encoded complement inhibiting protein that is a homologue of VCP in the cowpox virus has been termed "inflammation modulatory protein" (IMP) (Miller et al., 1997, *Virology,* 229:126-133). IMP has been shown in a mouse air-pouch model to significantly reduce the influx of inflammatory cells and drastically diminish the tissue damage elicited by cowpox virus infection (Kotwal et al., 1998, *Mol. Cell. Biochem.,* 185:39-46). A VCP homologue also has been identified in monkeypox virus (Schelkunov et al., 1998, *Virology,* 243:432-460), variola virus, and smallpox. Various Poxvirus-encoded complement inhibiting proteins are functionally identical and, therefore, can be interchanged.

Nucleic Acids, Polypeptides, and Related Methods

The following terms are used to describe the sequence relationships between two or more nucleic acids or polypeptides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a sequence, wherein the sequence in the comparison window may include additions or deletions (i.e., gaps) compared to the reference sequence (which does not include additions or deletions) for optimal alignment of the two sequences. Generally, the comparison window is at least 10 contiguous nucleotides or amino acids in length, and optionally can be 20, 30, 40, 50, 60, 100, or longer. Those of skill in the art understand that to avoid a high similarity to a reference sequence due to inclusion of gaps in the sequence a gap penalty is typically introduced and is subtracted from the number of matches.

Figure 1:
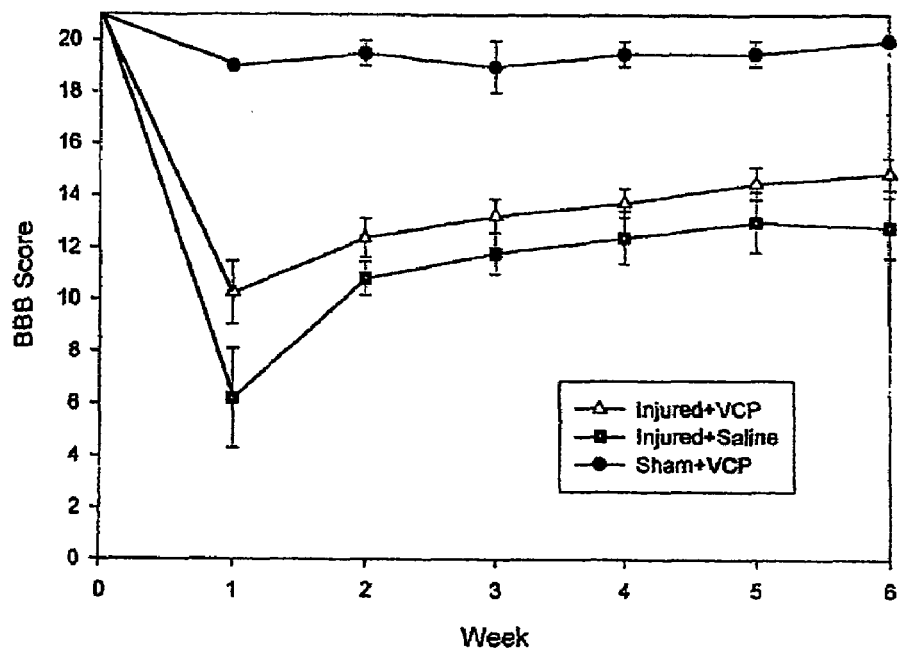
FIG. 1 depicts graphs showing BBB scores for left hind limbs of injured and control rats (FIG. 1A), and BBB scores for right hind limbs of injured and control rats (FIG. 1B).
Figure 1:
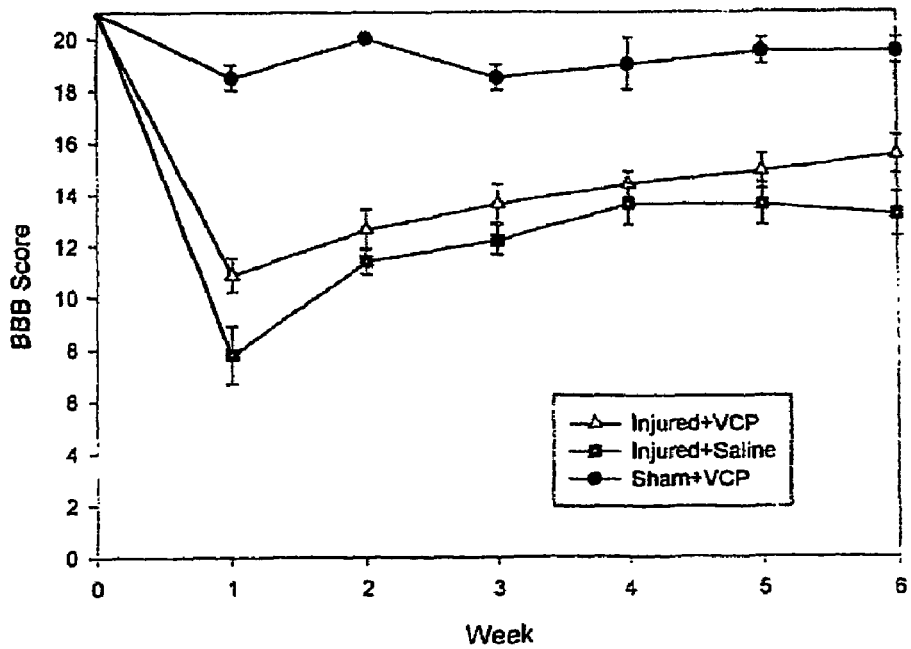

Methods of alignment of sequences for comparison are well known in the art. Thus, the determination of percent identity between any two sequences can be accomplished using a mathematical algorithm. Examples of such mathematical algorithms are the algorithm of Myers and Miller (1988, *CABIOS*, 4:11); the local homology algorithm of Smith et al. (1981, *Adv. Appl. Math.*, 2:482); the homology alignment algorithm of Needleman and Wunsch (1970, *J. Mol. Biol.*, 48:443); the search-for-similarity-method of Pearson and Lipman (1988, *PNAS USA*, 85:2444); the algorithm of Karlin and Altschul (1990, *PNAS USA*, 87:2264), modified as in Karlin and Altschul (1993, *PNAS USA*, 90:5873).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988, *Gene*, 73:237), Higgins et al. (1989, *CABIOS*, 5:151), Corpet et al. (1988, *Nucl. Acids Res.*, 16:10881), Huang et al. (1992, *CABIOS*, 8:155), and Pearson et al. (1994, *Meth. Mol. Biol.*, 24:307). The ALIGN program is based on the algorithm of Myers and Miller, supra. The BLAST programs of Altschul et al. (1990, *J. Mol. Biol.*, 215:403; and 1997, *Nuc. Acids Res.*, 25:3389) are based on the algorithm of Karlin and Altschul supra.

Software for performing BLAST analyses is publicly available through the National Center for Biotechnology Information (ncbi.nlm.nih.gov on the World Wide Web). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence can be less than about 0.1, less than about 0.01, or less than about 0.001.

To obtain gapped alignments for comparison purposes, Gapped BLAST (in BLAST 2.0) can be utilized as described in Altschul et al. (1997, *Nuc. Acids Res.*, 25:3389). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (L) of 10, a cutoff of 100, M=5, N=−4, and a comparison of both strands. For amino acid sequences, the BLASTP program uses as defaults a wordlength (W) of 3, an expectation (1) of 10, and the BLOSUM62 scoring matrix. See the World Wide Web at ncbi.nln.nih.gov. Alignment may also be performed manually by inspection.

For purposes of the present invention, comparison of nucleotide sequences for determination of percent sequence identity to the promoter sequences disclosed herein can be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the alternative program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide includes a sequence with at least 70%, 71%, 72%, 73%, 74%, 75%, 76%, 77%, 78%, 79%, 80%, 81%, 82%, 83%, 84%, 85%, 86%, 87%, 88%, 89%, at least 90%, 91%, 92%, 93%, or 94%, or 95%, 96%, 97%, 98% or 99%, sequence identity to the reference sequence over a specified comparison window. Optimal alignment may be conducted using the homology alignment algorithm of Needleman and Wunsch (1970, supra). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984, *Anal Biochem.*, 138:267); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and the desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration can be increased so that a higher temperature can be used. An extensive guide to the hybridization of nucleic acids is found in Tijssen (1993, *Laboratory Techniques in Biochemistry and Molecular Biology Hybridization with Nucleic Acid Probes*, Part 1, Chapter 2, "Overview of principles of 15 hybridization and the strategy of nucleic acid probe assays," Elsevier, N.Y.). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 66×SSC at 40° C. for 15 minutes. For short probes (e.g., about 10 to 50 nucleotides), stringent conditions typically involve salt concentrations of less than about 1.5 M, or about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37 C, and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the invention described herein includes methods using polypeptides that are substantially identical to VCP or to a homologue thereof.

The invention also includes proteins with substitutions of at least one amino acid residue in the polypeptide. Amino acid substitutions falling within the scope of the invention include those that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

Substitution of like amino acids can also be made on the basis of hydrophilicity. As detailed in U.S. Pat. No. 4,554, 101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In such changes, the substitution of amino acids whose hydrophilicity values can be within ±2, within ±1, or within ±0.5.

In one embodiment of the invention, a Poxvirus-encoded complement inhibiting protein has a conservative amino acid substitution, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Exemplary substitutions include those in Table 1.

TABLE 1

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr; Ala; Leu |
| Thr | Ser; Ala |
| Trp | Tyr |
| Tyr | Trp; Phe |
| Val | Ile; Leu |

Poxvirus-encoded complement inhibiting proteins (e.g., VCP and homologues thereof), molecules that are substantially identical to such proteins, and such proteins that contain one or more substitutions, can all be assayed for functionality using methods known in the art. The ability of a protein to inhibit the complement cascade or to inhibit cellular infiltration can be determined using pharmacological models that are well known in the art. For example, see The Merck Manual, $17^{th}$ Ed., Merck Research Laboratories, Whitehouse Station, N.J., USA, 1999, page 1022; Kotwal et al., 1990, *Science,* 250:827; and Rosengard et al., 2002, *PNAS USA,* 99:8808-13. Specifically, the functionality of a Poxvirus-encoded complement inhibiting protein can be confirmed by its ability to inhibit complement-mediated lysis of sheep erythrocytes in a hemolysis microassay (Kotwal et al., 1990, supra). Such proteins also can evaluated for their effectiveness in treating spinal cord injury.

Formulations and Administration

Salts of carboxyl groups of a Poxvirus-encoded complement inhibiting protein may be prepared in the usual manner by contacting the polypeptide with one or more equivalents of a desired base such as, for example, a metallic hydroxide base, e.g. sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of a Poxvirus-encoded complement inhibiting protein may be prepared by utilizing an N-acyl protected amino acid for the final condensation, or by acylating a protected or unprotected polypeptide. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like.

Formyl-methionine, pyroglutamine and trimethyl-alanine may be substituted at the N-terminal residue of the polypeptide. Other amino-terminal modifications include aminooxypentane modifications.

Acid addition salts of the polypeptide or of amino residues of the polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

A Poxvirus-encoded complement inhibiting protein, including its salts, can be administered to a patient. Administration of a Poxvirus-encoded complement inhibiting protein in accordance with the present invention may be in a single dose, in multiple doses, and/or in a continuous or intermittent manner, depending, for example, upon the recipient's physiological condition, whether the purpose of the administration is therapeutic or prophylactic, and other factors known to skilled practitioners. The administration of a Poxvirus-encoded complement inhibiting protein may be essentially continuous over a pre-selected period of time or may be in a series of spaced doses. The amount administered will vary depending on various factors including, but not limited to, the condition to be treated and the weight, physical condition, health, and age of the patient. Such factors can be determined by employing animal models or other test systems that are available in the art.

To prepare a Poxvirus-encoded complement inhibiting protein, the desired protein is synthesized or otherwise obtained and purified as necessary or desired. A Poxvirus-encoded complement inhibiting protein can be adjusted to the appropriate concentration, and optionally combined with other agents. The absolute weight of a Poxvirus-encoded complement inhibiting protein included in a unit dose can vary.

One or more suitable unit dosage forms including a Poxvirus-encoded complement inhibiting protein can be administered by a variety of routes including topical, oral, parenteral (including subcutaneous, intravenous, intramuscular and intraperitoneal), rectal, dermal, transdermal, intrathoracic, intrapulmonary and intranasal (respiratory) routes. A Poxvirus-encoded complement inhibiting protein can also be administered directly into a patient's spinal cord area, for example, into the intraparenchymal area of the spinal cord.

The formulations may, where appropriate, be conveniently presented in discrete unit dosage forms, and may be prepared by any of the methods well known to the pharmaceutical arts. Such methods may include the step of mixing a Poxvirus-encoded complement inhibiting protein with liquid carriers, solid matrices, semi-solid carriers, finely divided solid carriers or combinations thereof, and then, if necessary, introducing or shaping the product into the desired delivery system. By "pharmaceutically acceptable" it is meant a carrier, diluent, excipient, and/or salt that is compatible with the other ingredients of the formulation, and not deleterious or unsuitably harmful to the recipient thereof. The therapeutic compounds may also be formulated for sustained release (for example, using microencapsulation, see WO 94/07529 and U.S. Pat. No. 4,962,091).

A Poxvirus-encoded complement inhibiting protein may be formulated for parenteral administration (e.g., by injection, for example, bolus injection or continuous infusion) and may be presented in unit dose form in ampoules, pre-filled syringes, small volume infusion containers, or in multi-dose containers. Preservatives can be added to help maintain the shelve life of the dosage form. A Poxvirus-encoded complement inhibiting protein and other ingredients may form suspensions, solutions, or emulsions in oily or aqueous vehicles, and may contain formulatory agents such as suspending, stabilizing, and/or dispersing agents. Alternatively, a Poxvirus-encoded complement inhibiting protein and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers and vehicles that are available in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add other ingredients such as antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and $\alpha$-tocopherol and its derivatives can be added.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions at a pH of about 7.0-8.0.

Furthermore, a Poxvirus-encoded complement inhibiting protein may also be used in combination with other therapeutic agents, for example, pain relievers, anti-inflammatory agents, antihistamines, and the like, whether for the conditions described or some other condition.

The present invention further pertains to a packaged pharmaceutical composition such as a kit or other container. The kit or container holds a therapeutically effective amount of a pharmaceutical composition for and instructions for using the pharmaceutical composition for treating a condition.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Example 1

VCP Treatment for Spinal Cord Injury

Applicants have discovered that treatment with vaccinia virus complement control protein (VCP) reduces inflammation and improves spinal cord integrity following spinal cord injury.

The efforts invested in spinal cord injury (SCI) research have increased dramatically over the course of the past decade. Due to recent advancements in the understanding of SCI pathophysiologic mechanisms, and to renewed public interest, a great deal of attention has been channeled into research concerning spinal cord injury and potential therapeutic strategies. SCI exploration languished until recently partly because of the complexity of the injury process following the initial mechanical trauma. It is now believed that multiple physiologic processes contribute to what has become known as the secondary injury phase, which begins within minutes of primary injury and can persist for years. Hemorrhage, ischemia-reperfusion, excitotoxicity, demyelination, calcium mediated injury, disturbances in mitochondrial function, apoptosis and necrosis of neurons and oligodendrocytes, and inflammation are all mechanisms currently thought to be involved in the exacerbation of primary injury.

The gross appearances of the VCP treated injured cords were quite revealing when compared to injured-control cords (saline injected). While the sham-VCP cords closely resembled normal uninjured cords, the injured-control cords were extremely bruised and displayed a great deal of liquefaction of the inner contents and deformation upon cutting of segments for removal. Surprisingly, the VCP-injured cords did not resemble the injured-control cords, but rather displayed structural integrity more akin to the sham-VCP cords. Bruising was much less severe in the VCP-treated injured cords than in the injured-control cords, and the VCP-treated injured cords displayed much less liquefaction upon dissection. These results indicate VCP administration limits lesion size and severity, leading to increased tissue sparing. Even a relatively small degree of neuronal sparing may have a significant effect upon improved functional recovery following SCI.

Behavioral tests indicate that VCP treatment promotes motor function recovery. The 21-point Basso-Beattie-Bresnahan (BBB) open-field locomotor scale is a commonly used test to analyze the recovery of hind-limb function over the course of several weeks after injury. Animals were scored once per week for a total of six weeks. Injured-VCP animals demonstrated a substantially higher BBB score at week one for both hind limbs when compared to injured-saline animals. While the gap between the two groups closed significantly after the first week, the average scores for injured-VCP animals remained consistently higher than the injured-saline throughout the six-week study. While the difference in scores for injured-VCP versus injured-saline at week one were not statistically significant, the results did indicate VCP can promote some degree of motor function recovery in the early stages of injury. Given that VCP injections were only given once immediately after injury and not multiple times throughout the six-week study, it is not surprising that the most substantial difference in scores was observed only within one week of injection.

The same animals subjected to the six-week BBB study were also analyzed at week six with the grid-walling test (Behrmann et al., 1994, *Exp. Neurol.*, 126:61-75), a less subjective analysis of hind-limb function. It was found that injured-VCP animals committed significantly fewer footfalls per evaluation period than did the injured-saline animals. These results were statistically significant, and demonstrated the BBB test should not be the only motor function assessment utilized when dealing with spinal cord injured animals. The BBB test relies on human graders to make subjective judgments concerning subtle, but quick hind-limb movements of three different joints (hip, knee, and ankle). These movements can be challenging, not only to observe, but to then categorize in a short time. The grid walking test requires human observers to simply record the number of times a single hind-limb is placed through the open squares of a grid apparatus, relying less upon subjective judgment. It was evident that, even though there was no statistically significant difference between VCP-treated and untreated animals according to the BBB test at week six, there was a clear motor function benefit displayed by VCP-treated animals when negotiating the grid test at the same time point. Thus, VCP possesses the ability to promote motor function recovery.

Based on the results reported herein, VCP is an effective therapeutic agent for the treatment of SCI, for example, traumatic SCI.

Example 2

Production and Purification of VCP

VCP was produced by the *Pichia pastolis* yeast expression system (Invitrogen, Carlsbad, Calif.) described previously (Murthy et al., 2001, *Cell*, 104:301-11; Smith et al., 2000, *J. Virol.*, 74:5659-5666). Purification of VCP was achieved through heparin HiTRAP (Pharmacia) column chromatography, with VCP elution attained with a gradient of NaCl (100 mM-1 M). VCP regularly eluted from the heparin column with the 400 mM fraction of NaCl. Presence of VCP was confirmed with SDS-PAGE and silver staining.

Example 3

Spinal Cord Injury Model

All procedures involving experimental animals were performed according to the guidelines of the University of Louisville Institutional Animal Care and Use Committee. Impact injury was induced using a weight-drop device developed at New York University (Gruner, 1992, *Neurotrauma*, 9:123-126; Basso et al., 1996, *Ex. Neurol.*, 139:244-256). Adult Sprague-Dawley rats weighing between 200-250 gm were anesthetized with pentobarbital (50 mg/kg, i.p.) and given prophylactic antibiotic injections (gentomycin sulfate, 15 mg/kg, sc.) if survival times were planned to exceed 48 hours. A laminectomy was performed at the T9-T10 level and the spinous processes of T8 and T11 were rigidly clamped in a spinal frame in order to stabilize the spine. The exposed dorsal surface of the cord was then subjected to a mild impact injury in which a 10 gm rod (2.5 mm in diameter) was dropped at a height of 12.5 mm and displaced the cord for a duration of 23 msec, using an NYU Impactor. The mild (12.5-gm/cm) severity was chosen because there is sufficient locomotor recovery to enable the rats to stand and walk approximately 6 weeks post-injury. The injury protocol used produces an anatomically consistent contusion lesion, which is reproducible between animals and results in immediate and complete hindlimb paralysis, with partial recovery over the course of 5-6 weeks post-injury (Basso et al., 1995, *J. Neurotrauma*, 12:1-21). The dura remained intact during injury induction. For animals not designated to receive post-injury intraparenchymal injections, muscles were then sutured with No. 4-0 silk thread and skin closed with clips. Animals designated to receive intraparenchymal injections were immediately subjected to the injection protocol described below, and wounds closed with sutures and clips as described previously. Sham-operated control animals received T9-T10 laminectomy without weight-drop injury.

Following surgery, animals were given 10 ml subcutaneous (sc) injections of 0.9% saline solution and placed on a heating pad (36.5-37.5° C.) until recovery from anesthesia. Animals were then placed in their cages with food and water easily accessible and returned to the animal-holding facilities where they were maintained and monitored until the designated time of sacrifice. For animals that received contusion injury, bladders were manually expressed twice daily until normal voiding was obtained (usually by 10-14 days).

Example 4

Spinal Cord Intraparenchymal Injections

The Kentucky Spinal Cord Injury Research Center at the University of Louisville has developed an effective method of injecting small proteins into the rat spinal cord parenchyma (Magnuson et al., 1999, *Exp. Neurol.*, 156:191-204). Borosilicate pipettes (1.2 μm O.D.) were pulled on a Sutter Electrode Puller (P-87) and beveled to 25 μm (WPI Beveler). The pipettes are pre-marked with 0.2-1.5 μl graduations and with short pressure pulses (0.5-100 ms, 5-20 psi), the device is capable of delivering as little as 0.2 μl of solution with great accuracy. The pipettes were lowered into the spinal cord using a stereotaxic apparatus. Immediately prior to each injection, the dura was delicately opened and reflected with a 30-gauge needle in order to allow access for the injection pipette. All experimental animals designated to receive intra-parenchymal injections were given two bilateral 5 μl injections, for a total of 10 μl per animal, of the desired solution at the visible T9 injury epicenter, or at the comparable site in uninjured control animals. The injection pipettes were placed 1.6 mm deep in the spinal cord tissue and 0.7 mm from the midline of the spinal cord. Immediately prior to injection, the pipettes were raised slightly (less than 1 mm) in order to provide a reservoir within the tissue in which the injected solution could pool. Each 5 μl injection was given gradually over a period of 5 minutes in order to avoid fluid pressure-induced tissue damage. Following injection, muscles were sutured and skin closed with clips. Control animals received injections of normal saline, while other animals received injections of VCP.

Example 5

Rat Perfusions

Animals were deeply anesthetized with intraperitoneal (i.p.) injections of 0.3 ml-0.4 ml pentobarbital and placed securely on a dissecting rack. Using surgical scissors, the diaphragm was punctured and the heart exposed. A perfusion needle was then inserted through the left ventricle, left atrium, and into the ascending aorta. A small puncture was then made in the right atrium in order to allow blood and other fluids to drain. Next, 200 ml-250 ml of 0.01 M PBS were pumped through the animals' circulatory system, followed by 400 ml-500 ml of 4% paraformaldehyde (Sigma, St. Louis, Mo.) in 0.01 M PBS. The animals were then dissected and spinal cord sections were removed using surgical scalpels and forceps, and placed in 4% paraformaldehyde overnight. Spinal cord sections were then placed in a solution of 25% sucrose in 0.01 M PBS and maintained at 4° C. until sectioning.

Example 6

Tissue Sectioning & ED-1 Immunostaining

Spinal cord tissue was placed on a metal platform, embedded in TBS tissue freezing medium (Triangle Biomedical Sciences, Durham, N.C.) in the desired orientation, and placed inside a Bright OTF Cryostat (Bright Instrument Co., Huntingdon, England) set at −20° C. The temperature of the tissue/tissue-freezing medium was allowed to equilibrate for a period of 30-45 minutes before sectioning. The section thickness was set to 20 μm and the tissue cut in cross-section or longitudinally. Tissue sections were immediately placed on Superfrost/Plus microscope slides (Fisher) and stored at 4° C.

Mounted sections were washed 3 times in 0.01 M PBS in order to remove the freezing medium. Next, 200 μl of block solution (0.01 M PBS/0.3% Triton/10% normal donkey serum) was added and allowed to incubate at room temperature for 1 hour. A solution of mouse antiED-1 antibody (Serotec, Raleigh, N.C.) was then mixed with block solution at a dilution of 1:200 and 200 μl added to each slide. Slides were incubated overnight at room temperature and washed in PBS 5 times on day 2. A solution of donkey anti-mouse-FITC (Jackson ImmunoResearch Labs, West Grove, Pa.) was mixed with the block solution (without donkey serum) at a dilution of 1:100 and 200 μl was added to each slide. The slides were shaken gently in a dark at room for 2 hours and washed in PBS 3 times. Slides were dried, mounted with Gel/Mount (Biomeda, Foster City, Calif.), and stored in the dark at 4° C. Stained tissue was viewed with an Eclipse TE 300 (Nikon, Melville, N.Y.) fluorescent microscope at magnifications of either 40× or 100×. Images were captured with a SPOT TR Color camera (Diagnostic Instruments, San Diego, Calif.) and processed with SPOT Advanced software.

Example 7

Assessment of Locomotor Function

The 21-point Basso-Beattie-Bresnahan (BBB) open-field locomotor scale developed at The Ohio State University was used to evaluate functional recovery (Basso et al., 1995, supra). The BBB involves placing the rats in an empty plastic wading pool and assessing the hindlimb movements over a time period of 4 minutes. Three investigators observed the animals' movements independently and a score for each animal was given based on the consensus of the investigators. Beginning one week post-surgery, animals were evaluated once per week for six weeks. The BBB scoring system evaluates all major motor groups of the hindlimbs, bladder function, and ability to ambulate. The 21-point scale generally follows the progression of recovery, with a score of 21 representing the characteristics of a normal animal.

The grid-walking test assesses an animal's ability to walk over a plastic mesh (thickness of 0.5 mm) with diamond-shaped openings (4.5×5 cm) pulled over a square metal frame (46 inches square) for a period of three minutes. The grid surface was raised 12-24 inches in height in order to provide a lateral view of hindlimbs above and below the grid surface. Two blinded investigators, with each investigator observing only the right or left hindlimb, recorded the number of hindlimb footfalls through the mesh. Footfalls were counted only if the hindlimb descended below the mesh to at least the hip (¾ of the limb). Multiple failed attempts to reposition the same limb at one particular location on the grid were not counted as additional footfall errors. Since animals with insufficient hindlimb recovery could not be used, the test was administered at six weeks post injury, a time point at which most injured animals were achieving a minimum score of 11 on the BBB scale. Statistical analysis was carried out using paired t-test.

Example 8

Gross Appearance of Injured VCP-Treated Spinal Cords

Before the excision of the injured VCP treated spinal cords, images of the exposed cords were captured with a 35 mm camera. The pictures were taken after the skin, musculature, and appropriate vertebrae had been removed. The cords had been cut into three sections (rostral, epicenter, and caudal) with surgical scissors, but were not otherwise manipulated. The pictures were taken to provide a record of the gross appearance of spinal cord integrity prior to removal from the animal. The uninjured cord (sham) received only an injection (~76 μg) of VCP. The integrity and appearance of the cord was very similar to that of a normal spinal cord. No bruising or discoloration was evident and upon cutting of the cord, there was neither liquefaction nor subsequent leakage of spinal cord tissue. While the integrity of the sham-VCP cord was excellent, the injured control cord was severely damaged. The epicenter section was bruised and discolored, with a significant degree of liquefaction and leakage of upon cutting, resulting in loss of structural integrity. Similar characteristics were observed in the cord segments immediately rostral and caudal to the epicenter. Conversely, the injured VCP treated cord was similar in appearance to the uninjured cord. The injured VCP cord displayed only slight bruising, but no liquefaction nor leakage of cord contents upon cutting, enabling the structural integrity of the epicenter segment to remain intact.

Example 9

Role of VCP in Altering Macrophage/Microglial Response Following SCI

The role of VCP in altering the macrophage/microglial response following injury was assessed with the ED-1 antibody, which is specific for a lysosomal antigen in activated macrophages/microglial cells. Spinal cord tissue obtained from animals at three different time points (48 hours, 7 days, and 14 days) was stained with ED-1. Initial results indicate that macrophage/microglial activation and/or influx is reduced at the 48 h time point in injured-VCP animals when compared to injured-saline animals. After 7 days, there appeared to be little difference in the overall amount of macrophage/microglial influx, although the staining is more intense in the central gray matter of the injured-VCP animals and more diffuse in the injured-saline animals. After 14 days, the staining was much more intense in the injured-saline animals, with only a small area of positive staining in the dorsal funiculus of the injured-VCP animals. Uninjured animals show little to no positive ED-1 staining.

Example 10

Role of VCP in Altering Motor Function Recovery Following SCI

The 21 point Basso-Beattie-Bresnahan (BBB) open-field locomotor scale and a grid walking test were the methods utilized to evaluate locomotor function recovery following SCI: The BBB rates the ability of an animal to use the hind limbs during ambulation. A score of 21 would indicate a completely normal animal, while a score of 0 would indicate no observable hind limb movement. BBB experiments involved sham-VCP (n=2), saline-injured (n=5), and injured-VCP animals (n=8) (FIG. 1). VCP animals received 5 μl bilateral injections (4.80 μg/μl) for a total of 48 μg per animal. Hind limbs were rated separately once per week for 6 weeks following injury. The average scores for sham-VCP animals remained nearly normal during the 6-week study, with the left hind limb fluctuating between 19 and 20 (FIG. 1A), and the right hind limb between 18.5 and 20 (FIG. 1B). The average scores of the saline-injured animals were significantly worse, with the left hind limb scoring a 6.2 at week 1, a 12.8 at week 6, and achieving a maximum of 13 at week 5. The right hind limb scores reached an initial 7.8 at week 1, a final score of 13.2 at week 6, and a maximum of 13.6 at weeks 4 and 5 (FIG. 1B). The average left hind limb scores of the injured-VCP animals began with a 10.3 at week 1 and ended with a maximum of 14.9 at week 6 (FIG. 1A). The right hind limb scores began with a 10.9 at week 1 and ended with a maximum of 15.5. The scores for both hind limbs of the injured-VCP animals were substantially higher at week 1, but at each week thereafter the increases were not statistically significant, even though a trend of consistently higher scores for the injured-VCP animals was apparent.

Figure 2:
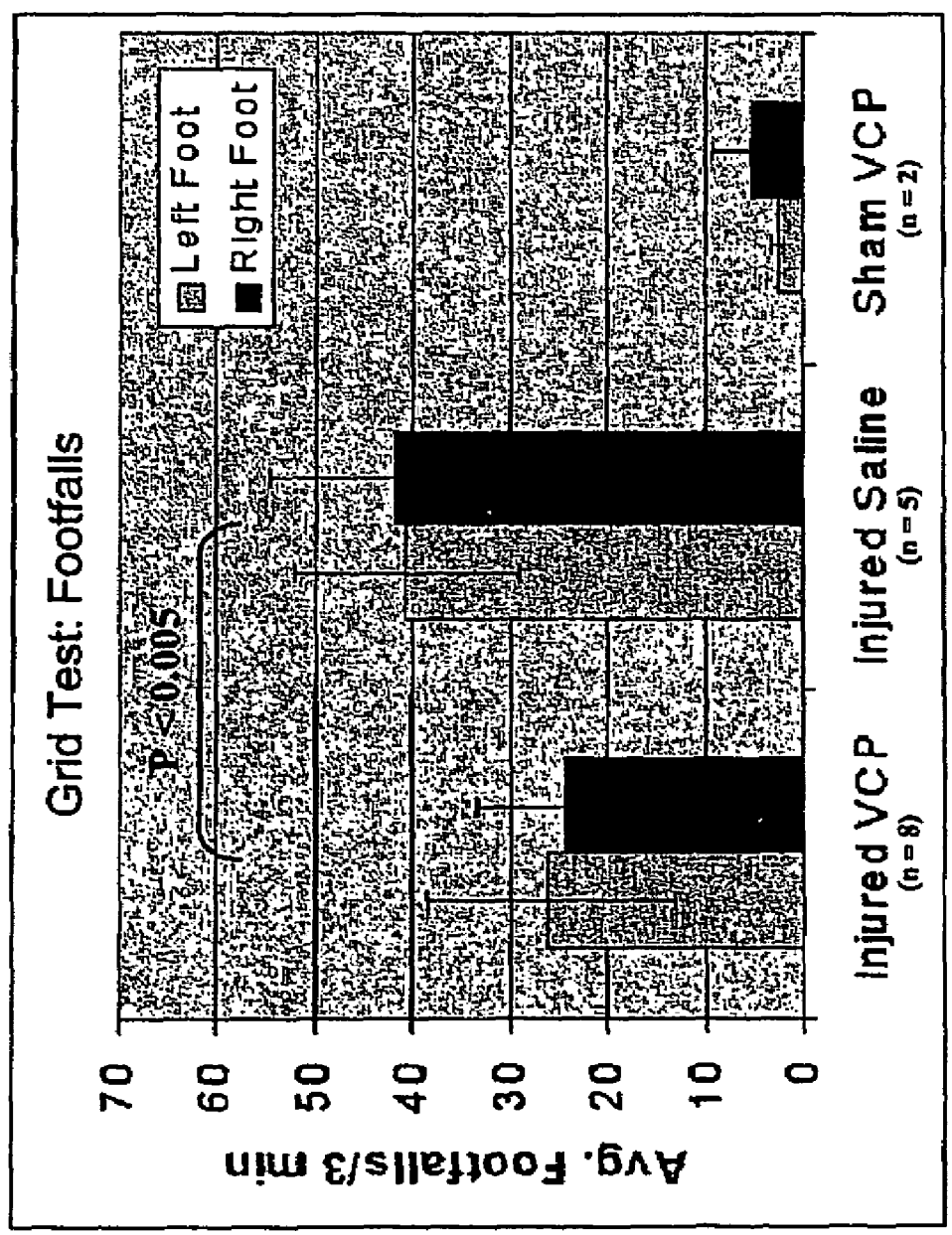
FIG. 2 depicts a graph showing grid walking test results (right and left hind foot) for injured saline injected, injured VCP treated, and sham VCP treated control animals six weeks after injury.

Following the conclusion of the 6-week BBB study involving the animals mentioned above, the same animals were subjected to a grid-walking test as a further measure of locomotor function recovery. The grid-walking test was administered only at week 6 and measured the number of times an animal's hind limbs slipped through (termed footfalls) a wire mesh during a 3-minute period of ambulation. The sham-VCP animals averaged only 3.75 footfalls, while the saline-injured animals averaged 41.2 footfalls, and the injured-VCP animals averaged 25.1 footfalls (FIG. 2). The differences between saline-injured animals and the injured-VCP animals were statistically significant ($p<0.005$) (FIG. 2).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for ameliorating at least one symptom associated with a spinal cord injury in a patient, comprising administering to the patient an effective amount of Poxvirus-encoded complement inhibiting protein and a pharmaceutically-acceptable carrier, wherein said administering is by injection at the site of injury, wherein the effective amount of the Poxvirus-encoded complement inhibiting protein ameliorates at least one symptom associated with the spinal cord injury.

2. The method of claim 1, wherein administration of the Poxvirus-encoded complement inhibiting protein delays the onset of at least one symptom of the spinal cord injury.

3. The method of claim 1, wherein the Poxvirus-encoded complement inhibiting protein is VCP.

4. The method of claim 3, wherein the VCP is recombinant VCP.

5. The method of claim 1, wherein the Poxvirus-encoded complement inhibiting protein is IMP.

6. The method of claim 1, wherein the Poxvirus-encoded complement inhibiting protein is monkeypox complement inhibiting protein.

7. The method of claim 1, wherein the Poxvirus-encoded complement inhibiting protein is variola virus complement inhibiting protein.

8. The method of claim 1, wherein the Poxvirus-encoded complement inhibiting protein is administered in multiple administrations.

9. The method of claim 1, wherein the Poxvirus-encoded complement inhibiting protein is administered in combination with at least one additional agent.

10. The method of claim 9, wherein the additional agent is selected from the group consisting of a nonsteroidal anti-inflammatory drug (NSAID), and a corticosteroid.

11. The method of claim 1, wherein administration of Poxvirus-encoded complement inhibiting protein reduces spinal cord damage associated with the spinal cord injury.

12. The method of claim 1, wherein administration of Poxvirus-encoded complement inhibiting protein reduces inflammation associated with the spinal cord injury.

13. The method of claim 1, wherein administration of Poxvirus-encoded complement inhibiting protein reduces loss of motor function associated with the spinal cord injury.

14. A method for ameliorating at least one symptom associated with a spinal cord injury in a patient, comprising administering to the patient an effective amount of Poxvirus-encoded complement inhibiting protein and a pharmaceutically-acceptable carrier, wherein the Poxvirus-encoded complement inhibiting protein is selected from the group consisting of VCP, IMP, monkeypox complement inhibiting protein, and variola virus complement inhibiting protein, wherein said administering is by injection at the site of injury, wherein the effective amount of the Poxvirus-encoded complement inhibiting protein ameliorates at least one symptom associated with the spinal cord injury.

\* \* \* \* \*

UNITED STATES PATENT AND TRADEMARK OFFICE
CERTIFICATE OF CORRECTION

PATENT NO. : 7,638,481 B2
APPLICATION NO. : 10/570402
DATED : December 29, 2009
INVENTOR(S) : Girish J. Kotwal Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this

Ninth Day of November, 2010

David J. Kappos
*Director of the United States Patent and Trademark Office*

SEQUENCE LISTING

<160> NUMBER OF SEQ ID NOS: 8

<210> SEQ ID NO 1
<211> LENGTH: 244
<212> TYPE: PRT

<213> ORGANISM: Vaccinia virus, Copenhagen strain

<400> SEQUENCE: 1

```
Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg
```

<210> SEQ ID NO 2
<211> LENGTH: 244
<212> TYPE: PRT
<213> ORGANISM: Vaccinia virus, western reserve strain

<400> SEQUENCE: 2

```
Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110
```

```
Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Thr Cys Ser Pro Gly Asn Thr Trp Lys Pro Glu Leu Pro
225                 230                 235                 240

Lys Cys Val Arg

<210> SEQ ID NO 3
<211> LENGTH: 244
<212> TYPE: PRT
<213> ORGANISM: Cowpox virus, Russian isolate from human patient

<400> SEQUENCE: 3

Cys Cys Pro Ile Pro Ser Arg Pro Ile Thr Met Lys Phe Lys Gly Thr
1               5                   10                  15

Val Glu Thr Asp Ala Asn Ser His Tyr Asn Ile Gly Asp Thr Ile Glu
                20                  25                  30

Tyr Leu Cys Leu Pro Gly Tyr Arg Lys Gln Lys Met Gly Pro Ile Tyr
            35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Thr Cys Ser Pro Gly Asn Thr Trp Gln Pro Glu Leu Pro
225                 230                 235                 240
```

Lys Cys Val Arg

<210> SEQ ID NO 4
<211> LENGTH: 244
<212> TYPE: PRT
<213> ORGANISM: Cowpox virus, Brighton strain

<400> SEQUENCE: 4

Cys Cys Thr Ile Pro Ser Arg Pro Ile Asn Met Lys Phe Lys Asn Ser
1               5                   10                  15

Val Gly Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Lys Cys Pro Ser Pro Arg Asp Ile Asp Asn Gly Gln Ile Asp Ile
65                  70                  75                  80

Gly Gly Val Glu Phe Gly Ser Ser Ile Thr Tyr Ser Cys Asn Ser Gly
                85                  90                  95

Tyr Gln Leu Ile Gly Glu Ser Lys Ser Tyr Cys Glu Leu Gly Tyr Thr
            100                 105                 110

Gly Ser Met Val Trp Asn Pro Glu Ala Pro Ile Cys Glu Ser Val Lys
        115                 120                 125

Cys Pro Ser Pro Pro Ser Val Thr Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Ile Val Cys Ser Gly Gly Glu Trp
                165                 170                 175

Ser Asp Pro Pro Thr Cys Gln Ile Val Lys Cys Pro His Pro Ser Ile
            180                 185                 190

Thr Asn Gly Tyr Leu Ser Ser Gly Phe Lys Arg Ser Tyr Ser His Asn
        195                 200                 205

Asp Asn Val Asp Phe Lys Cys Arg His Gly Tyr Lys Leu Ser Gly Ser
    210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 5
<211> LENGTH: 244
<212> TYPE: PRT
<213> ORGANISM: Variola virus, Bangladesh strain

<400> SEQUENCE: 5

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly His Leu Asp Ile

```
                 65                  70                  75                  80
Gly Gly Val Asp Phe Gly Ser Ser Ile Thr Tyr Ser Cys Asn Ser Gly
                    85                  90                  95

Tyr Tyr Leu Ile Gly Glu Tyr Lys Ser Tyr Cys Lys Leu Gly Ser Thr
                100                 105                 110

Gly Ser Met Val Trp Asn Pro Lys Ala Pro Ile Cys Glu Ser Val Lys
                115                 120                 125

Cys Gln Leu Pro Pro Ser Ile Ser Asn Gly Arg His Asn Gly Tyr Asn
                130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro His Pro Thr Ile
                180                 185                 190

Leu Asn Gly Tyr Leu Ser Ser Gly Phe Lys Arg Ser Tyr Ser Tyr Asn
                195                 200                 205

Asp Asn Val Asp Phe Thr Cys Lys Tyr Gly Tyr Lys Leu Ser Gly Ser
210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 6
<211> LENGTH: 244
<212> TYPE: PRT
<213> ORGANISM: Variola major virus, Indian strain

<400> SEQUENCE: 6

Cys Cys Thr Ile Pro Ser Arg Pro Ile Asn Met Thr Phe Lys Asn Ser
1               5                   10                  15

Val Glu Thr Asp Ala Asn Ala Asn Tyr Asn Ile Gly Asp Thr Ile Glu
                20                  25                  30

Tyr Leu Cys Leu Pro Gly Tyr Arg Lys Gln Lys Met Gly Pro Ile Tyr
                35                  40                  45

Ala Lys Cys Thr Gly Thr Gly Trp Thr Leu Phe Asn Gln Cys Ile Lys
            50                  55                  60

Arg Arg Cys Pro Ser Pro Arg Asp Ile Asp Asn Gly His Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Tyr Lys Ser Tyr Cys Lys Leu Gly Ser Thr
                100                 105                 110

Gly Ser Met Val Trp Asn Pro Lys Ala Pro Ile Cys Glu Ser Val Lys
                115                 120                 125

Cys Gln Leu Pro Pro Ser Ile Ser Asn Gly Arg His Asn Gly Tyr Asn
                130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro His Pro Thr Ile
                180                 185                 190

Leu Asn Gly Tyr Leu Ser Ser Gly Phe Lys Arg Ser Tyr Ser Tyr Asn
```

```
                195                 200                 205
Asp Asn Val Asp Phe Thr Cys Lys Tyr Gly Tyr Lys Leu Ser Gly Ser
    210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 7
<211> LENGTH: 244
<212> TYPE: PRT
<213> ORGANISM: Variola minor virus, alastrim Garcia strain

<400> SEQUENCE: 7

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly His Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Tyr Lys Ser Tyr Cys Lys Leu Gly Ser Thr
            100                 105                 110

Gly Ser Met Val Trp Asn Pro Lys Ala Pro Ile Cys Glu Ser Val Lys
        115                 120                 125

Cys Gln Leu Pro Pro Ser Ile Ser Asn Gly Arg His Asn Gly Tyr Asn
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro Tyr Pro Thr Ile
            180                 185                 190

Leu Asn Gly Tyr Leu Ser Ser Gly Phe Lys Arg Ser Tyr Ser Tyr Asn
        195                 200                 205

Asp Asn Val Asp Phe Thr Cys Lys Tyr Gly Tyr Lys Leu Ser Gly Ser
    210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 8
<211> LENGTH: 244
<212> TYPE: PRT
<213> ORGANISM: Monkeypox virus, human patient from Zaire

<400> SEQUENCE: 8

Tyr Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30
```

-continued

```
Tyr Leu Cys Leu Pro Gly Tyr Arg Lys Gln Lys Met Gly Pro Ile Tyr
        35              40              45

Ala Lys Cys Thr Gly Thr Gly Trp Thr Leu Phe Asn Gln Cys Ile Lys
    50              55              60

Arg Arg Cys Pro Ser Pro Arg Asp Ile Asp Asn Gly Gln Leu Asp Ile
65              70              75              80

Gly Gly Val Asp Phe Gly Ser Ser Ile Thr Tyr Ser Cys Asn Ser Gly
            85              90              95

Tyr His Leu Ile Gly Glu Ser Lys Ser Tyr Cys Glu Leu Gly Ser Thr
            100             105             110

Gly Ser Met Val Trp Asn Pro Glu Ala Pro Ile Cys Glu Ser Val Lys
        115             120             125

Cys Gln Ser Pro Pro Ser Ile Ser Asn Gly Arg His Asn Gly Tyr Glu
    130             135             140

Asp Phe Tyr Ile Asp Gly Ser Ile Val Thr Tyr Ser Cys Asn Ser Gly
145             150             155             160

Tyr Ser Leu Ile Gly Asn Ser Gly Val Met Cys Ser Gly Gly Glu Trp
            165             170             175

Ser Asn Pro Pro Thr Cys Gln Ile Val Lys Cys Pro His Pro Thr Ile
            180             185             190

Ser Asn Gly Lys Leu Leu Ala Ala Phe Lys Arg Ser Tyr Ser Tyr Asn
        195             200             205

Asp Asn Val Asp Phe Lys Cys Lys Tyr Gly Tyr Lys Leu Ser Gly Ser
    210             215             220

Ser Ser Ser Thr Cys Ser Pro Gly Asn Thr Trp Lys Pro Glu Leu Pro
225             230             235             240

Lys Cys Val Arg
```